(12) United States Patent
Teo

(10) Patent No.: US 6,168,564 B1
(45) Date of Patent: Jan. 2, 2001

(54) STEERABLE TRANSDUCER ARRAY FOR INTRACARDIAL ULTRASONIC IMAGING

(75) Inventor: Tat-Jin Teo, Sunnyvale, CA (US)

(73) Assignee: Sci-Med Life Systems, Inc., Maple Grove, MN (US)

( * ) Notice: Under 35 U.S.C. 154(b), the term of this patent shall be extended for 0 days.

(21) Appl. No.: 09/165,808

(22) Filed: Oct. 2, 1998

(51) Int. Cl.$^7$ .................................. A61B 8/00; A61B 8/12
(52) U.S. Cl. ............................ 600/443; 600/463; 600/467
(58) Field of Search .................................... 600/443, 447, 600/459, 462–463, 466–467

(56) References Cited

U.S. PATENT DOCUMENTS

| | | | |
|---|---|---|---|
| 4,180,790 | * 12/1979 | Thomas | 367/7 |
| 4,334,432 | * 6/1982 | Gill | 73/602 |
| 4,542,653 | 9/1985 | Liu | 73/626 |
| 4,550,607 | 11/1985 | Maslak et al. | 73/626 |
| 4,699,099 | 10/1987 | Maslak et al. | 73/626 |
| 5,651,366 | 7/1997 | Liang et al. | 128/662.06 |
| 5,680,863 | * 10/1997 | Hossach et al. | 600/459 |
| 5,784,336 | 7/1998 | Gopinathan et al. | 367/123 |

FOREIGN PATENT DOCUMENTS

WO 97/01768    1/1997  (WO) .

OTHER PUBLICATIONS

Gattzke et al., "Electronic Scanner of a Phased–Array Ultrasound Transducer," Hewlett–Packard Journal, Dec. 1983, pp. 13–20.

Prof. Albert Macovski, Medical Imaging Systems, Chapter 10, "Ultrasonic Imaging Using Arrays," Prentice–Hall, 1983.

* cited by examiner

Primary Examiner—Francis J. Jaworski
(74) Attorney, Agent, or Firm—Townsend and Townsend and Crew LLP

(57) ABSTRACT

In an ultrasonic imaging system, a transducer array structure, preferably a linear one-dimensional array on a catheter, is provided wherein the direction of a beam is controlled by a preselected, linear delay profile implementing a linear portion of a beam forming equation so that the array is effectively curved electronically. Beam forming is effected independently of the steering. An active aperture is provided by which a beam is steered according to linear array techniques. The active aperture comprises selected adjacent subsets of transducer elements of the array structure. The delay profile may be implemented by delay lines to each transducer element or by any preselected delay elements whereby the flatness or curvature of the array structure is matched and so that beam steering can be implemented by simple translation of the aperture along the transducer array. The pitch or separation between the transducer elements may be uniform or varied. Varied pitch permits sparser spacing of transducer elements along portions of the array structure. A quadratic portion of a beam forming equation is implemented in a beam former to control focus of the elements of the active aperture at each position of the active aperture.

23 Claims, 2 Drawing Sheets

STEERABLE TRANSDUCER ARRAY FOR INTRACARDIAL ULTRASONIC IMAGING

BACKGROUND OF THE INVENTION

This invention relates to intracardial ultrasonic imaging, particularly to a one-dimensional linear transducer array useful for detecting ultrasonic signals in real time in an intracardial environment, i.e., within the heart chambers, wherein a transducer array is employed.

Transducer arrays are employed to provide transmit ultrasonic signals and to collect data for reconstruction of an image from the ultrasonic artifacts reflecting off of features.

Scanning transducer arrays are known such as those described an article by Gattzke et al., "Electronic Scanner of a Phased-Array Ultrasound Transducer," Hewlett-Packard Journal, December 1983, pp. 13–20., and in a text by Prof. Albert Macovski, Medical Imaging Systems, Chapter 10, "Utrasonic Imaging Using Arrays," Prentice-Hall, 1983. A phased array acoustic imaging system with an active aperture has been described in U.S. Pat. No. 4,550,607 issued to Maslak et al. Nov. 5, 1985.

Two parameters are important in phased array transducers: beam steering and beam focussing. The current state of the art requires that transducer elements be spaced at about one-half wavelength of the center frequency of excitation along an axis in order for the resultant beam to be steerable off normal from the axis. It is known that undesired grating lobes manifest in directions other than the steered direction, especially where the steered direction is away from the normal axis and where the spacing exceeds one-half wavelength.

As is known in the art, such as Chapter 10 of the Macovski text, the field pattern of a linear array in the near field has a linear phase factor and a quadratic phase factor. Structures have been suggested to eliminate the quadratic term to simplify processing. Heretofore, structures have not been satisfactory, because of difficulties in maintaining control of the beam formation, steering and scanning.

In some applications, it is not necessary to steer a beam. For example, a linear array on a straight, flat axis does not require steering if the regions of investigation are normal to the array. Thus, an image may be generated by translating an active aperture between the array and the target along the axis of the array so that all radiated and received ultrasonic signals are normal to the array. In these cases, the spacing of the elements can typically be as large as one wavelength or more and still not have unacceptable grating lobes. On the other hand, the disadvantage of such a linear array is that a rectangular image size is governed by the transducer aperture which is built from the image lines, where the active aperture defines a beam width. To allow for larger image size while retaining a small transducer aperture, the transducer array is typically curved such that a convex surface directs the ultrasound beam in a divergent fashion to over a larger field of view. Requiring that the array be curved limits the flexibility of a transducer array. There are circumstances where bending of a transducer array, particularly in an enclosed chamber such as the heart cavity, is undesirable. What is needed is a mechanism whereby a transducer array can be used both to steer and to focus with minimal interaction between steering control and focus control so that real-time imaging can be achieved.

SUMMARY OF THE INVENTION

According to the invention, in an ultrasonic imaging system, a transducer array structure, preferably a linear one-dimensional array on a catheter, is provided wherein the beam steering is controlled by a preselected delay profile implementing a linear portion of a beam forming equation so that the array is effectively curved electronically, thus avoiding the need to curve the transducer array physically, as may be undesirable in such an application as intra-cardial imaging. An active aperture is provided for beam-steering, the aperture comprising selected adjacent subsets of transducer elements of the array structure. The preselected delay profile may be implemented by delay lines to each transducer element or by any preselected delay pattern selected to match the desired flatness or curvature of the array structure. The beam translation and steering can be implemented by simple activation of that portion of the array forming the active aperture, with the delay profile across the entire transducer array invoking the steering of the beam. The pitch or separation between the transducer elements may be uniform or varied. Varied pitch permits sparser spacing of transducer elements along portions of the array structure. A quadratic portion of the beam forming equation is implemented in a beam former to control focus of the elements of the active aperture at each position of the active aperture.

One of the advantages of this invention is that a phased array beam former can be implemented like a simple linear array beam former. A delay profile implements the linear portion of the beam forming equation for steering, while focussing is effected substantially independently by control of the quadratic portion of the beam forming equation. Because of relaxed requirements on the phased array, fewer elements are needed in the array, particularly in the center, since beams need only be steered using the linear portion of the beam-forming equation at the edges of the array.

The invention will be better understood by reference to the following detailed description in conjunction with the accompanying drawings.

DESCRIPTION OF SPECIFIC EMBODIMENTS

Figure 1:
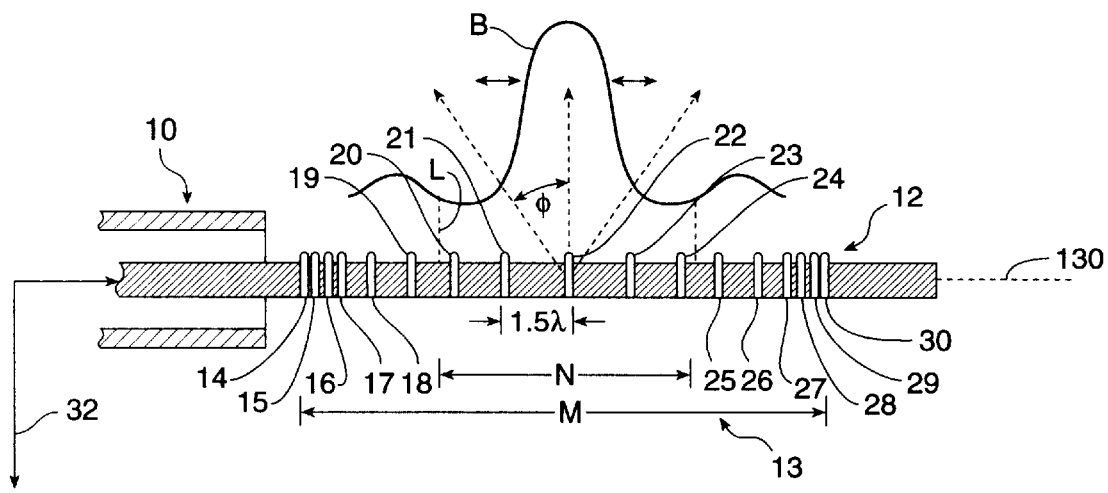
FIG. 1 is a side view depiction of one type of transducer array in a catheter according to the invention.

Referring to FIG. 1 there is shown a catheter apparatus 10 having a transducer array 12 coaxially disposed along an axis 130 within the catheter 10. A plurality of transducer elements 14-30 are spaced along the axis of the array 12 at separations which may either be uniform or, as shown, may vary with position. Uniform pitch of ½ wavelength is a specific embodiment. The positions or pitch in a variable pitch array are at about 1½ wavelengths at the center frequency of ultrasonic excitation of interest to a minimal separation of about ½ wavelength at the edges 14 and 30. In a specific embodiment the transducer array may have 128 elements at a pitch of ½ wavelength or 100 microns for a 7.5 MHz linear transducer, assuming the speed of sound in tissue is 1.54 mm/$\mu$sec.

A conduit 32 through the catheter 10 from the proximal end of the array 12 carries electrical signals of each transducer element 14-30 in the array 12, the number of elements in a transducer head 13 being equal to M. (Other leads may also be included in the conduit.) The number of active elements at any one time is N, a number less than M. To reduce the number of leads which must be mechanically accommodated, a first in-line multiplexer 36 of order of at least M by N is disposed between the conduit 32 and a feed conduit 40. A control subsystem 34 (FIG. 2) is coupled to the array 14-30 via the conduit 40.

According to the invention, a beam B is synthesized by providing selective adjacent activation of active elements excited according to a varied delay profile, and the aperture is translated along the transducer array by exciting successive groups of N elements. Beam forming (focus) is effected by fixed phase control in a control subsystem 34. If the delay profile of the activated elements N is symmetric, i.e., the activate elements are centered around a symmetric delay profile, the beam is normal to the array. If the delay profile of the activated elements is asymmetric, i.e., the beam so formed is translated by the translation of the active aperture so that the activated elements are around an asymmetric portion of the delay profile the resultant beam will be at an angle to the tangent of the axis 130 without change to the electronic beam forming profile of the resultant beam. In a specific embodiment, N=64 elements of M=128 elements form the initial aperture of about 6.4 mm.

Figure 2:
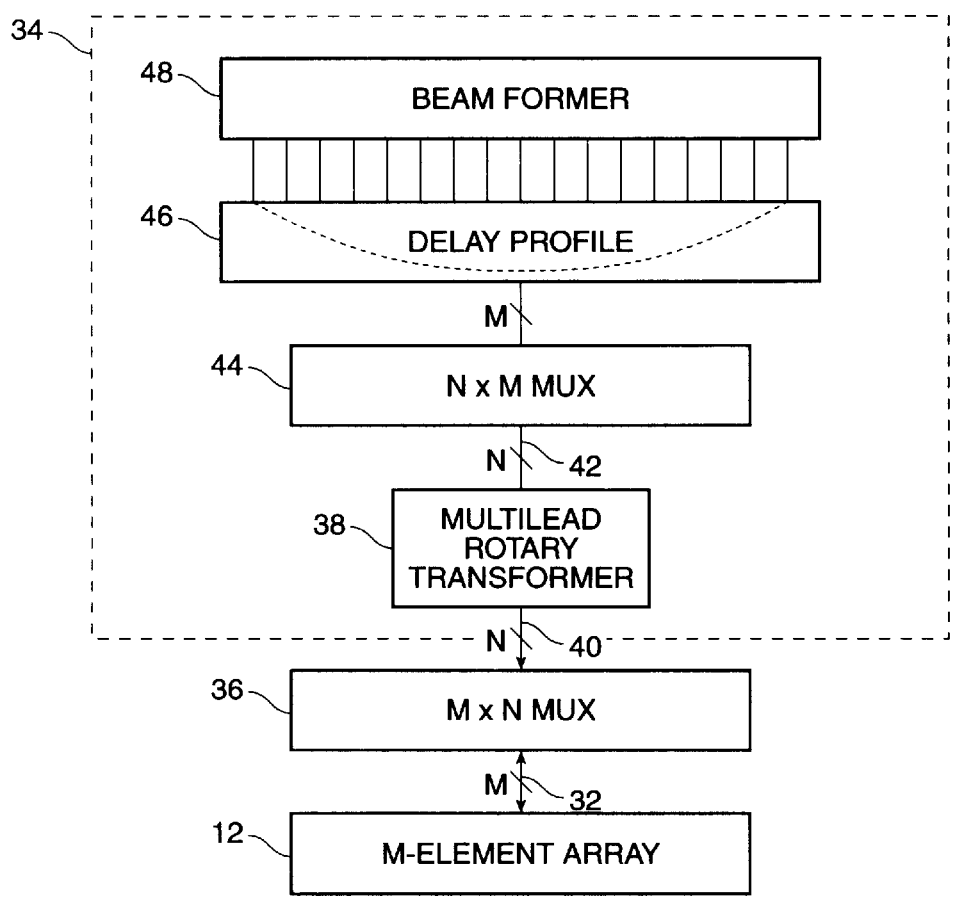
FIG. 2 is a block diagram of one embodiment of a system according to the invention.

FIG. 2 is a block diagram of the array 12 coupled via the conduit 40 to the control system 34, which is external to the subject under observation. The conduit 40 is coupled to a multi-lead rotary transformer 38. The transformer 38 may be a set of concentric slip ring contacts allowing the conductors of the secondary conduit 40 to rotate freely and signals to pass to a bus 42 to a second multiplexer 44 of order N by M or in other words, complementary to the first multiplexer 36.

The second multiplexer 44 provides parallel connections for a delay profile unit 46, which is preferably a symmetric fixed delay profile specific to the selected imaging geometry of interest. For a fixed delay profile, delay lines of varying length may be suitable, including for example bucket-brigade CCD delay lines. The delay profile unit 46 is coupled to a beam former 48 which implements the dynamic quadratic delay profile of a beam forming equation. In such a configuration only the dynamic quadratic delay profile for focussing needs to be implemented by an external controller 48.

Two types of delay profiles are contemplated. A steering component based on the linear portion of a beam forming equation may be implemented with a preselected delay profile which is specific to a particular imaging geometry, i.e., the curvature of the transducer delay. In such a case, the structure for beam forming may be simplified relative to that of a conventional phased array beam forming structure so that it more closely resembles a linear array beam forming structure. In this implementation, the transducer elements may be uniformly spaced. The next delay profile implementing the quadratic portion of the beam forming equation may be dynamic in echo reception in that it differs for each position along the direction of the returning echoes. Nevertheless, for transmission the same set of quadratic delays can be used for the different positions of the active aperture along the transducer array.

While the delay profile computation for each position and each convergence may be complex, the implementation is simplified when the two components, linear and quadratic, are separated. Even though the implementation of a static quadratic delay for transmission and a dynamic quadratic delay for reception, are suggested in the art, the implementation of the steering portion of beam forming using a preselected delay profile removes the need to provide a physical curvature of a transducer array, which is undesirable in some applications.

Figure 3:
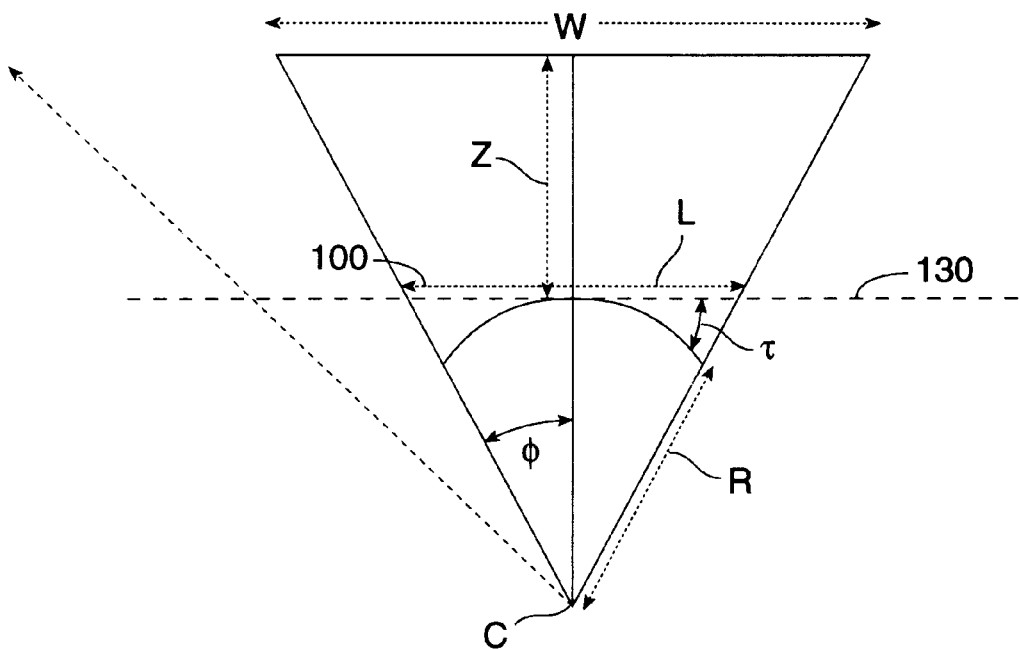
FIG. 3 is a diagram for illustrating beam steering and beam forming according to the invention.

Referring to FIG. 3, the implementation of an aperture for an electronic curved array is illustrated. An aperture 100 along axis 130 of diameter L, which is equal to the average spacing between array elements times the number of elements (N) within the aperture, illuminates an image width W at a depth Z from the plane of the transducer. The angle $\phi$ measured from the normal of the plane of the aperture 100 from the center C of curvature of the gain profile is related to the delay $\tau$ at each transducer element. The aperture 100 of extent L, with image width W at depth Z, the angle $\phi$ and the radius of curvature R are related by the expressions:

$$\phi = \arctan[(W/2-L/2)]/Z$$

$$R = (L/2)\cot(\phi)$$

In a typical system the transducers are operated with a center frequency of 7.5 MHz, producing a wavelength $\lambda$ in human tissue of about 205 $\mu$m (where speed of sound in human tissue is 1.54 mm/$\mu$sec). The pitch in a typical uniform pitch phased array system with steered beams is $0.5\lambda/\sin(2\phi)$. An active aperture consisting of N elements across aperture L of the M elements is implemented by step-wise exciting each of the N elements to generate various image lines making up the image, with delay $\tau$ in activation selected to correspond to the segment of the delay profile in which the element resides.

The delay profile can be reasonably approximated in a beam forming equation with a linear term for steering and a quadratic term for focus. The linear term in $\tau$ is: $\tau x = \phi x/R$, where x is the distance (up to L/2) from the normal along the aperture. The quadratic term is based on a phase shift $\psi$ set at $\frac{1}{2}\lambda$ so that terms cancels to produce a quadratic term in $\tau$ of: $\tau x = -\psi x^2/R$. This latter term is a dynamically changed for implementing focus independently of the scan angle over reasonable angles of interest, i.e., +/−45 degrees. In an implementation where the pitch is fixed the delay profile is incremented in fixed increments. In an implementation where the pitch changes with angle, the delay profile is incremented according to the change in position along the array.

In one implementation, if the image width of 10 cm is desired at a depth of 8 cm, the half sector angle would be about 28 degrees, with a radius of curvature of about 11 mm. If uniform half wavelength pitch is implemented, the beam forming is much simplified. Beam steering can be effected using the delay profile to achieve a much larger field of view without the need for physical array curvature.

In a second implementation, the transducer elements may be spaced at varied pitch, with smaller pitch at the edges and larger pitch up to 1.5–2 wavelengths near the center, thus reducing the number of elements and channels. However, the beam former would no longer operate as a simplified linear beam former. Instead it would be a more complex phased array beam former.

The invention has been explained with reference to specific embodiments. Other embodiments will be evident to those of ordinary skill in the art. It is therefore not intended that this invention be limited, except as indicated by the appended claims.

What is claimed is:

1. An ultrasonic array apparatus for activation of scanning ultrasonic radiation within a cavity comprising:
   (a) a plurality of transducing elements spaced relative to one another along a row;
   (b) means for providing a fixed activation signal delay to each one of said transducing elements according to a fixed delay profile that implements a linear phase factor of a radiation pattern, said fixed delay profile comprising a longer fixed delay at the ends of said row than at the center of said row; and (c) active aperture means operative to sequentially activate selected adjacent subsets of said transducing elements, whereby activation of said active aperture means invokes a steering deflection of said radiation pattern in directions defined by said fixed delay profile.

2. The apparatus according to claim 1 wherein said apparatus further comprises a catheter and said row of transducing elements is sized and adapted to reside along a nominally straight portion of said catheter.

3. The apparatus according to claim 2 wherein said transducing elements are spaced from one another at a fixed pitch.

4. The apparatus according to claim 2 wherein said transducing elements are spaced from one another at a varied pitch having a minimum spacing of about ½ wavelength at the nominal wavelength of an ultrasonic excitation signal.

5. The apparatus according to claim 1 wherein said fixed delay profile further implements a quadratic phase factor in order to focus said radiation pattern upon activation of said active aperture means.

6. The apparatus according to claim 5 wherein said transducing elements are spaced from one another at a varied pitch having a minimum spacing of about ½ wavelength at the nominal wavelength of an ultrasonic excitation signal.

7. The apparatus according to claim 6 wherein the minimum spacing is at the ends of said row and wherein maximum spacing is at the center of said row.

8. The apparatus according to claim 5 wherein said means for providing a fixed activation signal delay comprise delay lines.

9. An ultrasonic array apparatus for activation of scanning ultrasonic radiation within a cavity comprising:

(a) a plurality of transducing elements spaced relative to one another along a row;

(b) a delay profile unit operative for delaying propagation of activation signals to each one of said transducing elements according to a fixed delay profile that implements a linear phase factor of a radiation pattern, said fixed delay profile comprising a longer fixed delay at the ends of said row than at the center of said row; and (c) a control subsystem to sequentially activate selected adjacent subsets of said transducing elements, whereby activation of said selected adjacent subsets invokes a steering deflection of said radiation pattern in directions defined by said fixed delay profile.

10. The apparatus according to claim 9 wherein said apparatus further comprises a catheter and said row of transducing elements is sized and adapted to reside along a nominally straight portion of said catheter transducer structure.

11. The apparatus according to claim 10 wherein said transducing elements are spaced from one another at a fixed pitch.

12. The apparatus according to claim 10 wherein said transducing elements are spaced from one another at a varied pitch having a minimum spacing of about ½ wavelength at the nominal wavelength of an ultrasonic excitation signal.

13. The apparatus according to claim 9 wherein said fixed delay profile further implements a quadratic phase factor in order to focus said radiation pattern upon activation of said selected adjacent subsets of said transducing elements.

14. The apparatus according to claim 13 wherein said transducing elements are spaced from one another at a varied pitch having a minimum spacing of about ½ wavelength at the nominal wavelength of an ultrasonic excitation signal.

15. The apparatus according to claim 14 wherein the minimum spacing is at the ends of said row and wherein maximum spacing is at the center of said row.

16. The apparatus according to claim 13 wherein said delay profile unit comprises delay lines.

17. A method for activating scanning ultrasonic radiation within a cavity comprising the steps of:

(a) disposing a plurality of transducing elements spaced relative to one another along a row within said cavity; and (b) sequentially activating selected adjacent subsets of said transducing elements with an activation signal to each such transducing element, wherein propagation of the activation signal to each such transducing element is delayed according to a fixed delay profile that implements a linear phase factor of a radiation pattern, said fixed delay profile comprising a longer fixed delay at the ends of said row than at the center of said row, to steer said radiation pattern in directions defined by said fixed delay profile.

18. The method according to claim 17 wherein said row of transducing elements is sized and adapted to reside along a nominally straight portion of a catheter.

19. The method according to claim 18 wherein said transducing elements are spaced from one another at a fixed pitch.

20. The method according to claim 18 wherein said transducing elements are spaced from one another at a varied pitch having a minimum spacing of about ½ wavelength at the nominal wavelength of an ultrasonic excitation signal.

21. The method according to claim 17 wherein said fixed delay profile further implements a quadratic phase factor in order to focus said radiation pattern.

22. The method according to claim 21 wherein said transducing elements are spaced from one another at a varied pitch having a minimum spacing of about ½ wavelength at the nominal wavelength of an ultrasonic excitation signal.

23. The method according to claim 22 wherein the minimum spacing is at the ends of said row and wherein maximum spacing is at the center of said row.

* * * * *